(12) United States Patent
Spiegelberg et al.

(10) Patent No.: US 12,390,624 B2
(45) Date of Patent: Aug. 19, 2025

(54) VALVE FOR PERMANENT IMPLANTATION, IN PARTICULAR FOR TREATMENT OF NORMAL PRESSURE HYDROCEPHALUS

(71) Applicants: Andreas Spiegelberg, Horgen (CH); UNIVERSITÄT BERN, Horgen (CH)

(72) Inventors: Andreas Spiegelberg, Horgen (CH); Jürgen Beck, Bolligen (CH)

(73) Assignee: UNIVERSITAT BERN, Bern (CH)

(*) Notice: Subject to any disclaimer, the term of this patent is extended or adjusted under 35 U.S.C. 154(b) by 776 days.

(21) Appl. No.: 17/418,861

(22) PCT Filed: Dec. 27, 2019

(86) PCT No.: PCT/EP2019/087124
§ 371 (c)(1),
(2) Date: Jun. 28, 2021

(87) PCT Pub. No.: WO2020/136278
PCT Pub. Date: Jul. 2, 2020

(65) Prior Publication Data
US 2022/0072285 A1    Mar. 10, 2022

(30) Foreign Application Priority Data
Dec. 28, 2018  (DE) ............... 10 2018 133 691.8

(51) Int. Cl.
*A61M 27/00* (2006.01)
*A61M 39/02* (2006.01)
(Continued)

(52) U.S. Cl.
CPC ...... *A61M 27/006* (2013.01); *A61M 39/0208* (2013.01); *A61M 39/24* (2013.01);
(Continued)

(58) Field of Classification Search
CPC ...... F16K 17/0406; F16K 17/06; F16K 17/12; A61M 2039/0235; A61M 27/006; A61M 39/0208; A61M 39/24
See application file for complete search history.

(56) References Cited

U.S. PATENT DOCUMENTS 2,977,980 A    4/1961  Axel
3,985,140 A    10/1976 Harris
(Continued)

FOREIGN PATENT DOCUMENTS

DE     693 13260       2/1998
DE     102009009880    10/2010
(Continued)

OTHER PUBLICATIONS

Fulcher, O. Hugh Enomoto, Francis: Some simple methods of treating communicating hydrocephalus. In: Surgical forum, Bd. 8, 1956, S. 516-521. ISSN 0071-8041.
(Continued)

*Primary Examiner* — Kai H Weng
(74) *Attorney, Agent, or Firm* — JMB Davis Ben-David

(57) ABSTRACT

The invention relates to an implantable valve (1) for a drainage system for discharging cerebrospinal fluid, comprising: a valve housing (10) extending along a valve axis (A), an inlet (2) and an outlet (3) as well as a valve housing (10) surrounding an interior space (4), a valve body assembly (600) arranged in the interior (4) and movably arranged in the interior space (4), a first valve seat (5), wherein the valve body assembly (600) is configured to abut the first valve seat (5) to close a flow connection between the inlet (2) and the interior space (4) of the valve housing (10), a second valve seat (7) which faces the first valve seat (5), wherein the valve body assembly (600) is configured to abut the second valve seat (7) to close a flow connection between the outlet (3) and the interior space (4) of the valve housing
(Continued)

(10), and a spring device (800) arranged in the interior space (4) which exerts a spring force on the valve body assembly (600) in the direction of the first valve seat (5).

20 Claims, 8 Drawing Sheets

(51) Int. Cl.
*A61M 39/24* (2006.01)
*F16K 17/04* (2006.01)
*F16K 17/06* (2006.01)
*F16K 17/12* (2006.01)

(52) U.S. Cl.
CPC .......... *F16K 17/0406* (2013.01); *F16K 17/06* (2013.01); *F16K 17/12* (2013.01); *A61M 2039/0235* (2013.01)

(56) References Cited

U.S. PATENT DOCUMENTS

| | | | |
|---|---|---|---|
| 4,675,003 A * | 6/1987 | Hooven | A61M 27/006 |
| | | | 604/9 |
| 4,682,625 A | 7/1987 | Christopher | |
| 4,945,947 A | 8/1990 | Westra et al. | |
| 5,336,166 A | 8/1994 | Sierra | |
| 5,366,166 A | 11/1994 | Schilz et al. | |
| 5,368,556 A | 11/1994 | Lecuyer | |
| 6,146,352 A * | 11/2000 | Bonnal | A61M 27/006 |
| | | | 604/9 |
| 7,513,883 B2 | 4/2009 | Glenn | |
| 2006/0224101 A1 | 10/2006 | Glenn | |
| 2006/0224102 A1 | 10/2006 | Glenn | |
| 2010/0056980 A1 | 3/2010 | Negre et al. | |
| 2014/0276348 A1 * | 9/2014 | Alan | A61M 39/24 |
| | | | 604/10 |
| 2014/0316325 A1 | 10/2014 | Jaber | |
| 2021/0244922 A1 * | 8/2021 | Sklar | A61M 27/006 |

FOREIGN PATENT DOCUMENTS

| | | |
|---|---|---|
| EP | 0 268 520 | 5/1988 |
| EP | 0414649 | 2/1991 |
| EP | 0617974 | 10/1994 |
| EP | 2221083 | 8/2010 |
| EP | 2253352 | 11/2010 |
| FR | 2685206 | 6/1993 |
| JP | S5230089 | 3/1977 |

OTHER PUBLICATIONS

Quincke, H.: Die Lumbalpunktion des Hydrocephalus. In: Berliner Klinische Wochenschrift, Bd. 28, 1891, H. 38, S. 929-933.—ISSN 0366-0974. (Quincke in Kie, "The lumbar puncture of hydrocephalus").

* cited by examiner

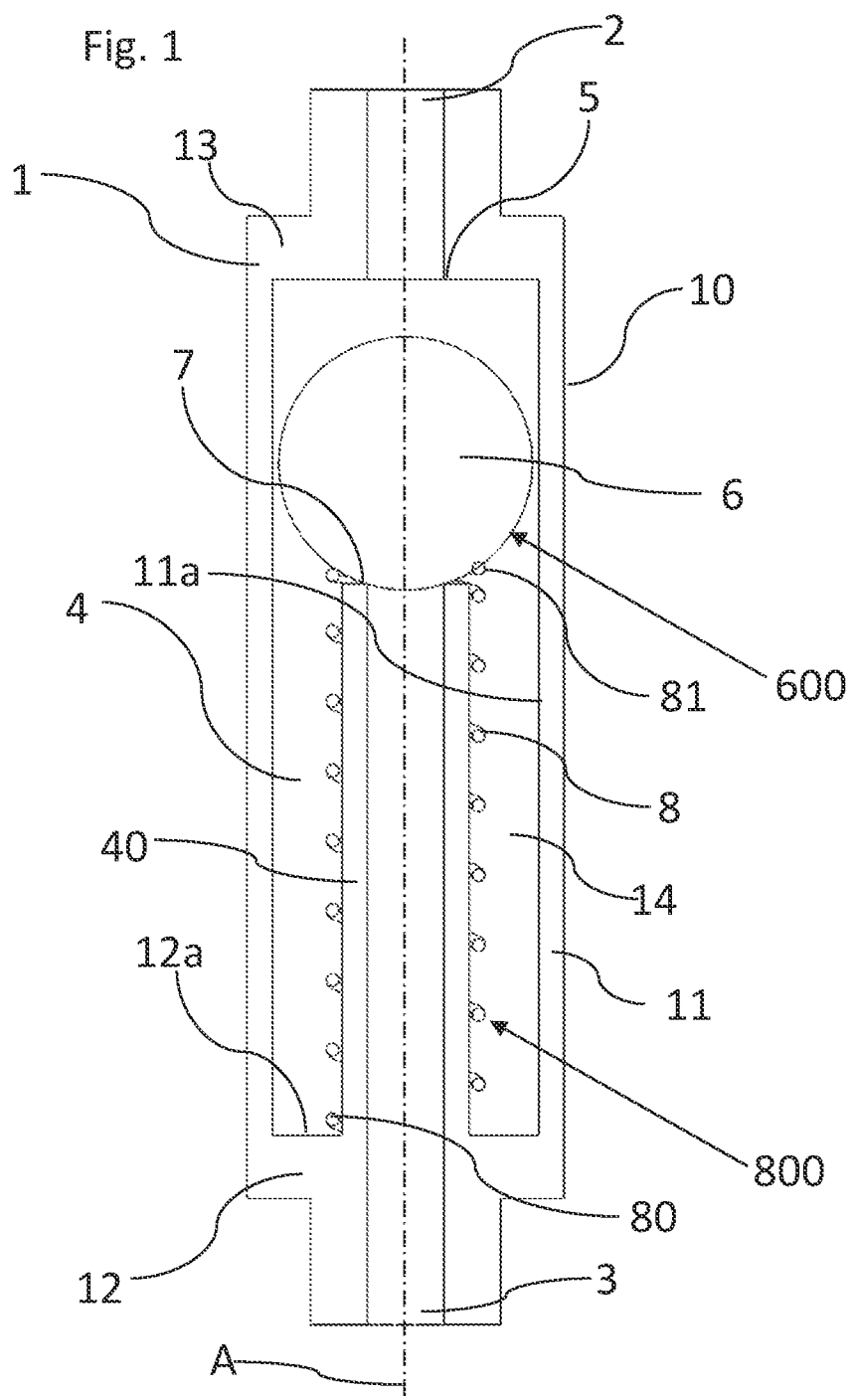

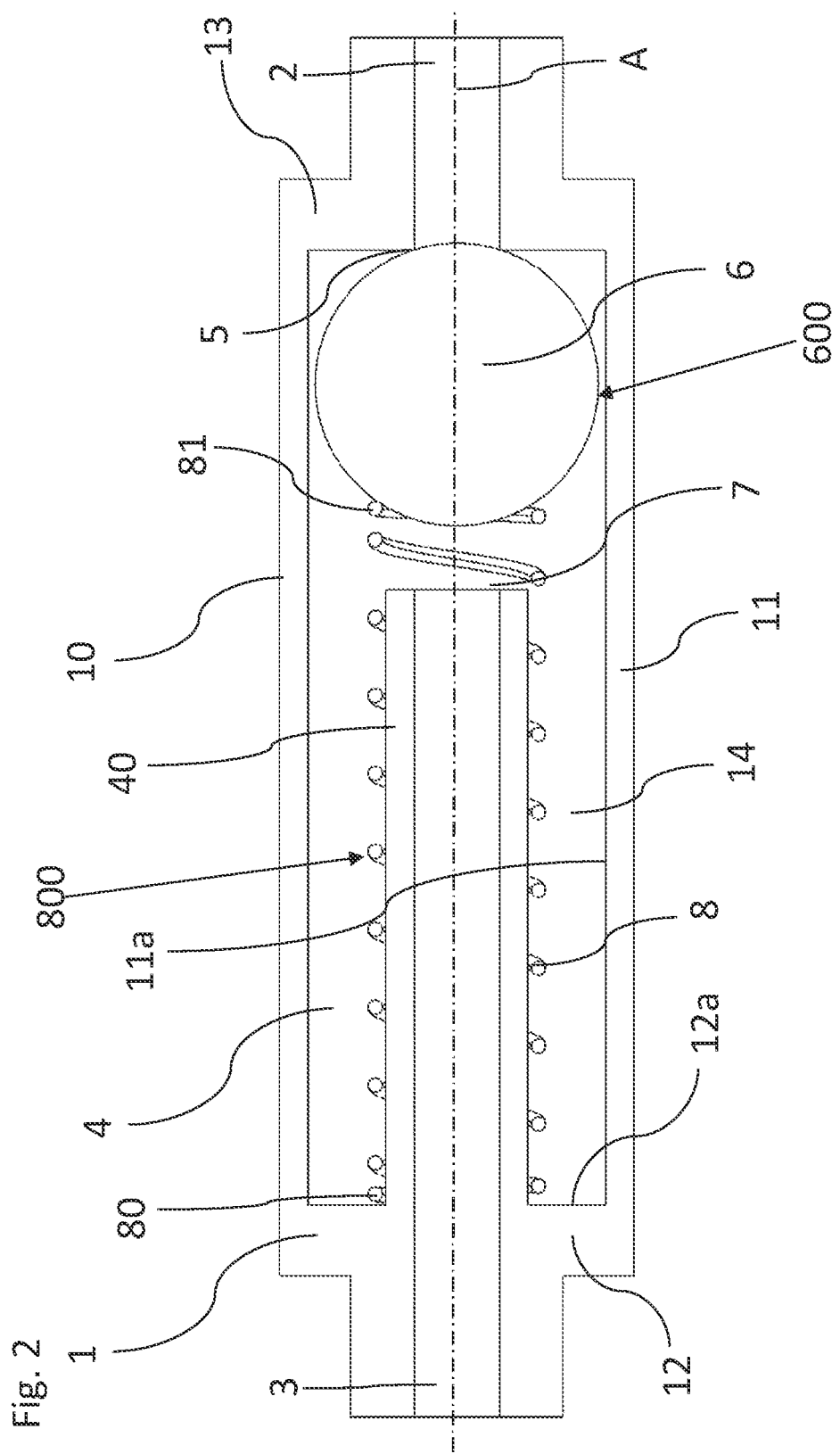

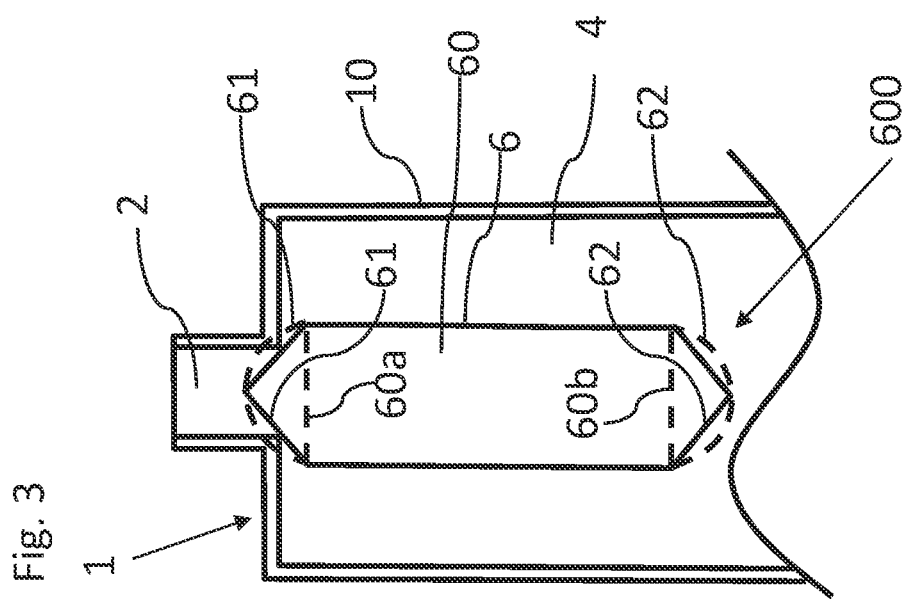
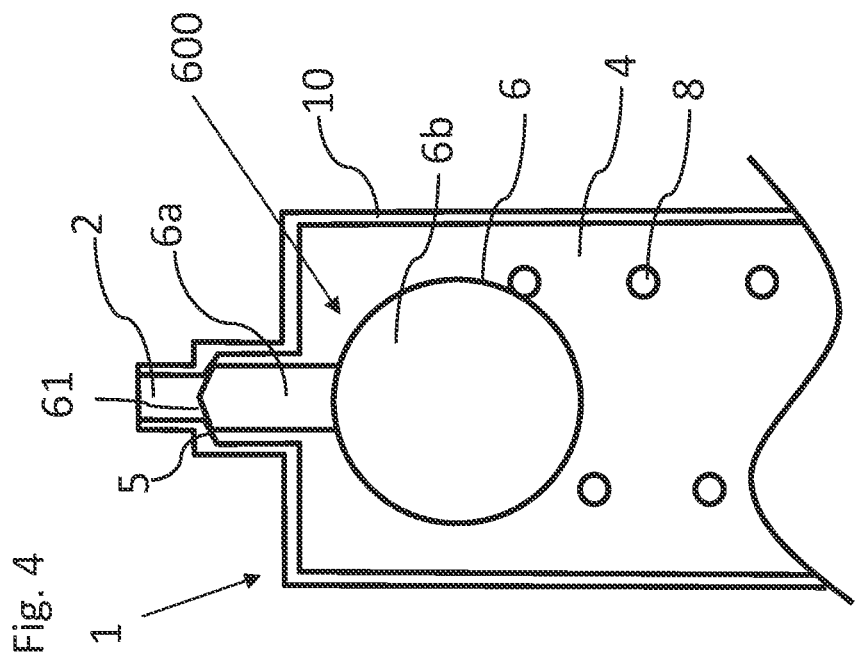

VALVE FOR PERMANENT IMPLANTATION, IN PARTICULAR FOR TREATMENT OF NORMAL PRESSURE HYDROCEPHALUS

CROSS-REFERENCE TO RELATED APPLICATIONS

This is the US National Stage of International Patent Application No. PCT/EP2019/087124 filed Dec. 27, 2019, which claims priority to German Patent Application No. 10 2018 133 691.8 filed Dec. 28, 2018.

The present invention relates to an implantable valve, in particular for permanent implantation for the treatment of hydrocephalus disease.

For the treatment of patients in whom there is an imbalance between the formation of cerebrospinal fluid (CFS) and the reabsorption of cerebrospinal fluid, the so-called hydrocephalus patients, drainage devices are used, which drain the cerebrospinal fluid (liquor cerebrospinalis) from the CSF-spaces of the brain into another body cavity. Fully implantable drainage devices usually consist of a ventricular catheter, the tip of which is placed in one of the patient's brain ventricles and is passed under the skin to a valve which prevents backflow of CSF and has a pressure relief function, and a peripheral catheter, that connects the outlet of the valve to a cavity in the body, for example the abdominal cavity. Such drainage devices are also referred to as shunt systems, the valves as shunt valves. After the first and simple drainage systems consisted only of a tube, shunt valves are used today to prevent overdrainage of CSF. CSF overdrainage, a well-known and feared complication of drainage systems, can lead to undesirable consequences such as poor concentration, headache and intracranial bleeding and even death.

A common operating principle of these overpressure valves is that, initially closed, they only open above a certain pressure, the set pressure, and only then drain CSF. This is to prevent overdrainage.

Valves suitable for such purposes are either equipped with a fixed threshold pressure that can be individually selected to suit the patient, or they are adjustable.

Furthermore, shunt valves are known in which the threshold pressure is automatically switched between a higher value in the upright position and a lower value in the horizontal position, or is continuously adjusted, depending on the body position. Various names are used for such kind of systems; in this description they are collectively referred to as gravity-compensated valves.

Shunt systems were originally developed for the treatment of such hydrocephalus diseases that are associated with the development of a clearly pathological overpressure. These are the large group of early childhood hydrocephalus patients and diseases acquired in old age in which the drainage and resorption process is disturbed, or in which one of the connections between the various CSF spaces is narrowed or closed.

A special group of hydrocephalus patients are the so-called normal pressure hydrocephalus patients (normal pressure hydrocephalus, NPH). With these, the mean pressure in the CSF is not pathologically increased. However, there are wave-like increases in pressure, particularly when sleeping and lying down. The treatment of this group of patients with drainage devices or shunt systems is fraught with particular difficulties: Because the mean pressure is not permanently increased, the setting or selection of the threshold pressure of the shunt valve is particularly critical. Threshold pressures that are only slightly too high lead to inadequate treatment results. On the other hand, these patients, who are adult and mobile, often experience hydrostatic overdrainage in the upright body position, which leads to serious complications. The use of gravity-compensated systems brings improvements, but the characteristics of the gravity compensation, just like the threshold pressure mentioned above, are very critical and must be adapted within narrow limits to the requirements of the individual patient.

For the treatment of NPH, attempts have been made to drain the CSF in the lumbar region from the subdural CSF-space under the dura mater (hard meninges) into the epidural space above the dura mater. The shunt systems that were used in these experiments differ significantly from the usual ventriculo-peritoneal shunt systems. Fulcher and Enomoto (OH Fulcher and F. Enomoto, "Some simple methods of treating communicating hydrocephalus," In Surgical forum, 1956, vol. 8, pp. 516-521) used an open piece of plastic tubing that was barbed so that it stayed in place. Quincke (H. Quincke, "Die Lumbalpunktion des Hydrocephalus," Berliner Klin. Wochenschrift, vol. 28, no. 38, pp. 929-933) punctured the subdural space and at the same time slit the dura so that a permanent drainage opening was created. Glenn (US020060224102, US020060224101, US000007513883) describes a system which has an inlet below the hard meninges, a flow regulator connected to it and an outlet connected to it for placement in the epidural space.

Furthermore, valves are generally known from EP0268520A2, EP2253352A1, JPS5230089A, U.S. Pat. No. 4,945,947A, US2010056980A1, EP0414649, U.S. Pat. Nos. 4,682,625, 2,977,980, FR 2 685 206 and U.S. Pat. No. 5,336,166, respectively.

Proceeding from this, the present invention is based on the aim of providing an improved implantable valve which is particularly suitable for shunt treatment of NPH with special consideration of the special requirements of these patients.

This aim is achieved by a valve and by a drainage device as described and claimed herein. Advantageous embodiments of these aspects of the invention are specified in the corresponding subclaims.

According to claim 1, an implantable valve for a shunt system for draining off CSF is disclosed, with:
  a valve housing which extends along a valve axis and has an inlet and an outlet as well as an interior space surrounded by the valve housing,
  a valve body assembly arranged in the interior space, which is movably arranged in the interior space, e.g., in the direction of the valve axis,
  a first valve seat, wherein the valve body assembly is configured to lie sealingly against the first valve seat in order to close a flow connection between the inlet and the interior space of the valve housing,
  a second valve seat, wherein the valve body assembly is configured to lie sealingly against the second valve seat in order to close a flow connection between the outlet and the interior space of the valve housing,
  a spring device arranged in the interior space and exerting a spring force on the valve body assembly in the direction of the first valve seat.

In particular, the valve body assembly is arranged in the direction of the valve axis between the two valve seats, the valve allowing CSF to pass through (from the inlet to the outlet) when the valve body assembly is not in sealing contact with either of the valve seats. This state of the valve is called open. If, on the other hand, the valve body assembly is in contact with one of the valve seats, the valve is closed and prevents the flow of CSF. Surprisingly, the treating physicians found that in NPH patients the single drainage of small volumes is sufficient to achieve a treatment success that lasts for days.

The valve according to the invention can ensure this because it is configured to be completely closed in an upright body position (or with a vertical valve axis) (e.g. in which gravity presses the valve body against the second valve seat) and is furthermore configured in a lying body position (or with a horizontal valve axis) to allow drainage at a (particularly low) response pressure (i.e. when the response pressure is open), but in particular prevents a backflow (in the sense of a non-return valve).

According to a preferred embodiment of the invention it is provided that the weight of the valve body assembly acts in the direction of the second valve seat when the valve housing is in a vertical position in which the valve axis runs vertically and the first valve seat is arranged above the second valve seat.

According to a further preferred embodiment of the invention it is provided that the weight of the valve body assembly in the vertical position of the valve housing is greater than the spring force, so that the valve body assembly rests against the second valve seat in a sealing manner.

According to a further preferred embodiment of the invention it is provided that the spring force is greater than a horizontal component of the weight of the valve body assembly when the valve housing is in a horizontal position in which the valve axis runs horizontally.

According to a further preferred embodiment of the invention it is provided that the second valve seat is closed by the valve body assembly when the valve housing is in an inclined position in which the valve axis encloses an angle with the vertical in the range from 0° to 40°, wherein, if the Angle exceeds 40°, the component of the weight force running parallel to the valve axis falls below the sum of pressure force and spring force, the valve body assembly moving (in particular abruptly) in the direction of the first valve seat and closing it (in particular without a transition).

According to a further preferred embodiment of the invention it is provided that the first valve seat is closed by the valve body assembly when the valve housing is in an inclined position in which the valve axis encloses an angle with the horizontal in the range from 0° to 40°. During this transition, the increasing weight force (parallel to the valve axis) and the pressure force increasing due to the change in position act simultaneously on the valve body assembly, so that a steep characteristic curve results. As the pressure force increases, the transition area becomes smaller and smaller, so that a problematically large transition area does not occur.

In particular, the present invention now functions for the first time according to a reverse principle compared to the principles set out at the beginning: the CSF drainage is only possible at low differential pressures (in the horizontal position). At higher differential pressures, which only occur in the vertical position, the valve is closed.

This mode of operation is particularly effective in preventing overdrainage. Because especially when there is a high-pressure gradient (e.g., when standing—here, about 30 cm to 60 cm of hydrostatic water column add up (in adults), from the head to the discharge point (spinal epidural space or abdominal cavity)), with the classic valve systems a lot of CSF drains and there is a risk of overdrainage.

The solution according to the invention therefore has the advantages that unphysiologically high drainage quantities can be avoided (the valve is only open or in the flow state at a lower pressure).

The valve according to the invention also forms a reliable switch (valve open/closed) using a large pressure difference of 30 cm to 60 cm water column (hydrostatic pressure difference from the transition from horizontal to upright in adults or transition from horizontal position to vertical position of the valve housing).

Furthermore, the pressure conditions in the outflow space (e.g., spinal subarachnoid space) and drainage (inflow) space (e.g., spinal epidural space or abdominal cavity) are advantageously at approximately the same level. There are only slight pressure gradients here. This implantation principle also reduces the risk of dangerous overdrainage.

Overall, the mode of operation of the valve according to the invention results in efficient drainage with significantly better protection against overdrainage.

According to one embodiment of the invention it is provided that the valve body assembly is formed by the first valve body.

According to an alternative embodiment of the invention it is provided that the valve body assembly has a second valve body, wherein the first valve body is configured to rest on the first valve seat, and the second valve body is configured to rest on the second valve seat and/or is heavier than the first valve body.

According to a further embodiment of the invention it is provided that the valve body assembly (in addition to the first valve body) has a second valve body and a third valve body, the first valve body being configured to rest on the first valve seat, and the third valve body being configured to rest on the second valve seat, and wherein the second valve body is heavier than the first valve body and/or than the third valve body. Furthermore, the valve can also have a plurality of second valve bodies, which are preferably arranged between the first and the third valve body.

Furthermore, according to one embodiment, it is preferably provided that the second valve body is arranged between the first and the third valve body and in particular is in contact with the first and the third valve body.

Furthermore, according to a preferred embodiment, it is provided that the respective valve body (i.e., the first and/or the second and/or the third valve body) is at least partially cylindrical, wherein in particular the respective valve body can be cylindrical.

According to a further embodiment of the invention it is provided that the respective valve body (or one of the valve bodies, in particular the first and/or the second and/or the third valve body) is spherical.

Furthermore, according to a preferred embodiment of the invention, it is provided that the respective valve body (or one of the valve bodies, in particular the first and/or the second and/or the third valve body) is cylindrical and has a first flat end surface which is to rest against the first valve seat or to rest against an adjacent valve body, as well as a second end face facing away from the first end surface, which is formed to rest on the second valve seat or to rest on an adjacent valve body.

Furthermore, according to a preferred alternative embodiment of the invention, it is provided that the respective valve body (or one of the valve bodies, in particular the first and/or the second and/or the third valve body) has a cylindrically designed central section that extends between a first end section and a second end section (the middle section connects the two end sections in particular in one piece), the first end section being designed to rest against the first valve seat or to rest against an adjacent valve body, and the second end section being designed to rest against the second valve seat or for contact with an adjacent valve body. The two end sections can each be curved or hemispherical or frustoconical or conical.

Furthermore, according to one embodiment of the invention, it is provided that a diameter of the second valve body is greater than a diameter of the first valve body and/or than a diameter of the third valve body of the valve body assembly.

Furthermore, according to a preferred embodiment of the invention it is provided that the respective valve body of the valve body assembly (or one of the valve bodies, in particular the first and/or the second and/or the third valve body) consists of a material that has a density of more than 10 g/cm$^3$.

Furthermore, according to a preferred embodiment of the invention it is provided that the respective valve body (or one of the valve bodies, in particular the first and/or the second and/or the third valve body) and/or the valve housing and/or the spring are made of a bio-compatible or body-compatible material, consists, or is coated with such a material. A bio-compatible material is, in particular, a material that has no negative influence on living beings, in particular human beings, in its environment.

According to a preferred embodiment of the invention it is provided that the respective valve body (or one of the valve bodies, in particular the first and/or the second and/or the third valve body) consists of one of the following substances or has one of the following substances: tungsten, a tungsten alloy, tungsten carbide, di-tungsten carbide, an alloy comprising tungsten carbide and/or di-tungsten carbide.

According to a preferred embodiment of the invention it is provided that the valve body consists of one of the following substances or has one of the following substances, silver, gold, platinum, tantalum or, in an alloy, one of the substances silver, gold, platinum, tantalum.

Furthermore, according to one embodiment of the invention, it is provided that the inlet of the valve is opposite the outlet of the valve in the direction of the valve axis, and/or that the second valve seat is opposite the first valve seat in the direction of the valve axis.

Furthermore, according to one embodiment of the invention, it is provided that the spring device has a first spring. In particular, the spring device can be formed by the first spring.

Furthermore, according to one embodiment of the invention, it is provided that the valve housing has a projection protruding into the interior space in the direction of the first valve seat.

According to one embodiment, it is provided that the projection forms an annular gap with a wall of the valve housing that runs around in the circumferential direction of the valve housing or with a circumferential inside of this wall.

According to one embodiment, this circumferential wall connects a first wall of the valve housing to a second wall of the valve housing opposite in the direction of the valve axis, wherein according to one embodiment the outlet is provided on the first wall and the inlet is provided on the second wall.

Furthermore, according to one embodiment of the invention, it is provided that the second valve seat is provided on an end section of the projection facing the first valve seat or the second wall. In particular, the projection surrounds a preferably elongated through-opening which forms the outlet of the valve. The second valve seat is formed, for example, by a circumferential end face of the projection which borders the through-opening at the end of the projection.

Furthermore, the second valve seat can also be formed by a circumferential section of the projection (e.g., in the form of a step).

Furthermore, according to one embodiment of the invention, it is provided that the first spring engages around the projection (and in particular is arranged in the annular gap). The first spring can in particular be designed as a helical spring.

Furthermore, it is provided according to one embodiment of the invention that the first spring is supported with a first end portion of the first spring on an inside of the first wall of the valve housing, from which the projection protrudes into the interior space of the valve housing.

Furthermore, according to one embodiment of the invention, it is provided that the valve assembly preferably consists of the at least one first valve body, the first spring contacting the at least one first valve body with a second end portion and the said spring force exerting on the first valve body in the direction of the first valve seat.

Furthermore, according to an alternative embodiment of the invention, it is provided that the valve assembly consists of the at least one first valve body and the second valve body or has these valve bodies, the first spring contacting with a second end section the second valve body and the spring force acts in the direction of the first valve seat on the second valve body, wherein the second valve body is configured to exert the spring force to the first valve body.

Furthermore, according to one embodiment of the invention it is provided that the valve assembly consists of the at least one first valve body, the second valve body and the third valve body or has these valve bodies, wherein the first spring contacts the second valve body with a second end portion and exerts a first part of the spring force in the direction of the first valve seat on the second valve body, wherein the second valve body is configured to exert the first part of the spring force to the first valve body.

Furthermore, according to one embodiment, it is provided here that the spring device has a second spring (wherein in particular the spring device is formed by the first and the second spring), the second spring being supported with a first end portion on an inside of the valve housing, and the second spring contacts the third valve body with a second end portion and exerts a second part of the spring force in the direction of the first valve seat on the third valve body, the third valve body being configured to exert the second part of the spring force via the second valve body to the first valve body.

Furthermore, according to one embodiment of the invention, it is provided that the outlet is formed by a longitudinally extending through-opening of the valve housing, the through-opening having a step. In particular, the through-opening is designed as a stepped bore.

Furthermore, according to one embodiment of the invention, it is provided that the second spring is supported with the first end section on the step.

Furthermore, according to one embodiment of the invention, it is provided that the second spring is arranged in the through-opening.

According to one embodiment, the second spring can also be a helical spring.

Furthermore, the second spring can be arranged coaxially with the first spring. The first spring can embrace the second spring.

The inlet of the valve is designed in particular as a through-opening in the second wall of the valve housing.

According to one embodiment, the first valve seat is formed by a circumferential edge region of the inlet or the corresponding through-opening, wherein that edge region borders the inlet or the through-opening.

Furthermore, the valve according to the invention is not restricted to a linear movement of the valve body. Thus, according to an alternative embodiment of the invention, it is provided that the valve body is pivotably mounted on the valve housing in the interior space, so that the valve body can be pivoted back and forth between the first and second valve seats, the spring (in particular the torsion spring) also attempting to move the valve body to the first valve seat.

Furthermore, the valve body can in principle be composed of several, in particular separate, bodies. For example, according to one embodiment it can be provided that the valve body has a first body and a second body, the first body being configured to rest on the first valve seat, and the second body being configured to rest on the second valve seat and/or being heavier than the first body. A large part of the weight of the valve body can be given by the second body, while the first body, for example, takes over the sealing on the first valve seat.

Furthermore, according to one embodiment of the invention, it can be provided that the valve body has a first body, one or more second bodies and a third body, the first body being configured to rest on the first valve seat, and the third body being configured to rest on the second valve seat, and wherein the second body or bodies is or are heavier than the first body and/or the third body.

According to a further embodiment of the valve according to the invention it is provided that the mass of the valve body assembly and the spring device or its spring force are selected so that the force of gravity on the valve body assembly does not affect the position of the valve body assembly relative to the first and second valve seats, so that in particular the said position with respect to the valve seats does not change when a spatial position of the valve axis of the valve changes.

According to a further aspect of the present invention, a drainage system is disclosed. According to this, the drainage device according to the invention for draining CSF has at least:
 a valve according to the invention,
 a first catheter (in particular a ventricular catheter) which has an end section that can be positioned in a brain chamber or the spinal CSF space of a patient and is in flow connection with the inlet of the valve so that CSF can enter the first catheter via the first end section, and
 a second catheter which is in flow connection with the outlet of the valve and has an end section which can be positioned in a cavity (e.g., abdominal cavity, epidural space) of the patient's body, so that CSF can exit from the second catheter via the end section into the cavity.

In particular, the end section of the first catheter thus has at least one inlet opening through which CSF can enter the first catheter. The end section of the second catheter also has at least one outlet opening through which CSF can exit from the second catheter. The drainage device according to the invention is particularly suitable for the treatment of normal pressure hydrocephalus disease. The inlet of the valve can be connected to the CSF space or subdural space of the patient in the region of the lumbar spine (the spinal CSF space) via the first catheter. In contrast, the outlet of the valve can be connected to the epidural space of the patient's lumbar spine via the second catheter.

Further embodiments, features and advantages of the present invention are to be explained below in the description of exemplary embodiments with reference to the figures.

FIG. 1 shows an embodiment of a valve according to the invention in a vertical position;

FIG. 2 shows an embodiment of a valve according to the invention in a horizontal position;

FIG. 3 shows different forms of a valve body of a valve according to the invention;

FIG. 4 shows an embodiment of a valve according to the invention with a valve body composed of two bodies;

Figure 5:
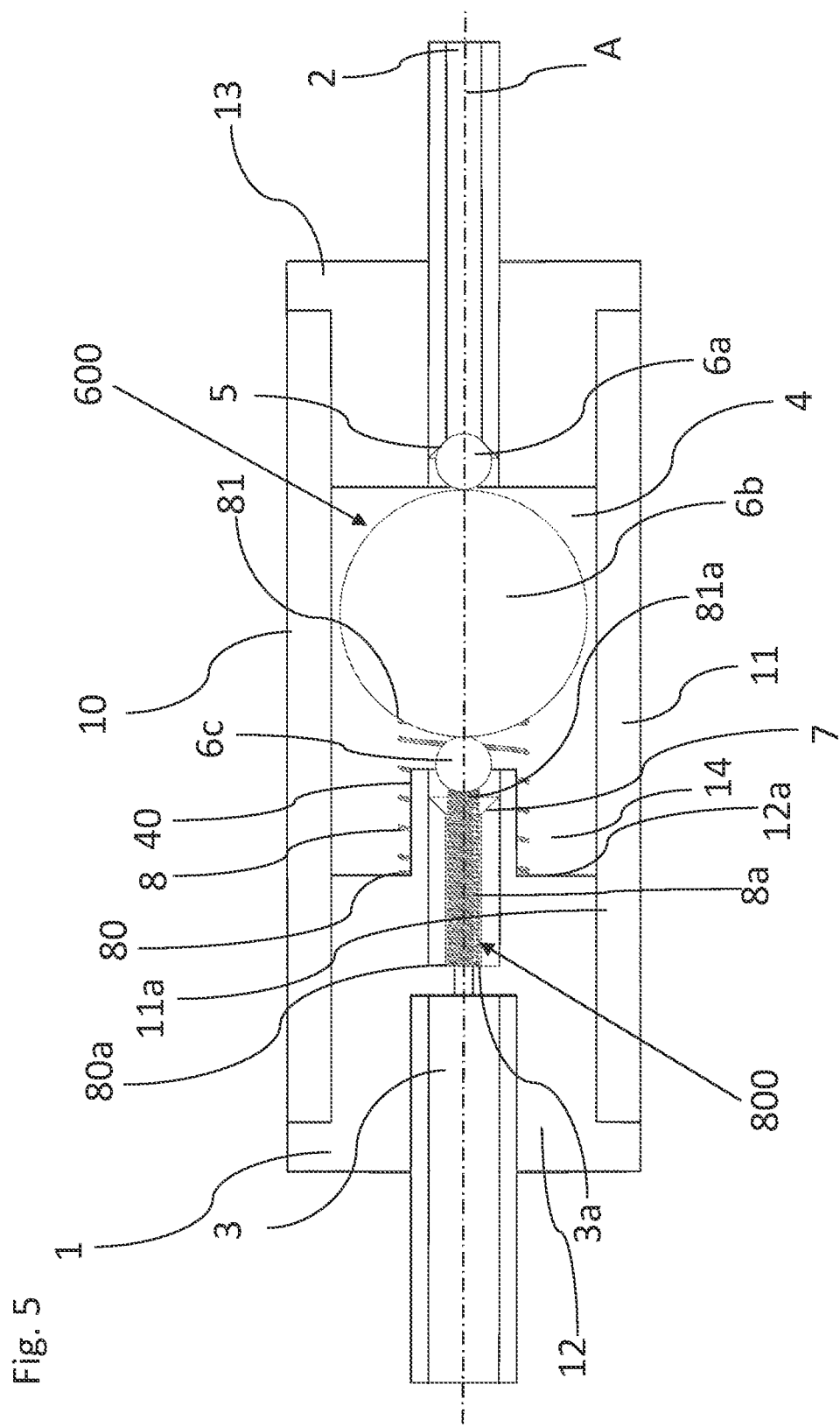
FIG. 5 shows an embodiment of a valve according to the Fig. invention with a valve body composed of three bodies.

In connection with FIG. 2, FIG. 1 shows a valve 1 according to the invention. The valve 1 has a valve housing 10 which has an inlet 2 and an outlet 3 and an interior space 4. The valve housing 10 extends along a valve axis A, the inlet 2 and the outlet 3 being opposite one another in the direction of the valve axis A.

A first valve seat 5 which can be closed by a valve body assembly 600 which here consists of a valve body 6 is located between the inlet 2 and the interior space 4. Furthermore, a second valve seat 7 which can also be closed by the valve body 6 is located between the interior space 4 and the outlet 3.

The valve housing 10 has a circumferential wall 11 which extends in the circumferential direction U of the valve housing 10 and which has a circumferential inside 11a facing the interior space 4. The circumferential wall 11 connects a first and a second wall 12, 13 of the valve housing 10 to one another, wherein in particular the outlet 3 is provided on the first wall 12 and the inlet 2 is provided on the second wall 13.

Furthermore, a protrusion 40 is provided in the interior space 4 in particular, which protrudes from an inside 12a of the first wall 12 in the direction of the first valve seat 5 or the second wall 13. The protrusion 40 forms an annular gap 14 with the inside 11a of the circumferential wall 11 of the valve housing 10.

The second valve seat 7 is provided in particular on an end of the protrusion 40 facing the first valve seat 5 or the second wall 13. The protrusion 40 surrounds in particular a longitudinally extending through-opening 3 which forms the outlet 3 of the valve 1. The second valve seat 7 is formed in particular by a circumferential end face 7 of the protrusion 40, which borders that through-opening or outlet 3 at the end of the protrusion 40.

Furthermore, the valve 1 preferably has a spring device 800, which here consists of a spring 8 which presses the valve body 6 against the first valve seat 5. The spring 8 and the dimensions and the material of the valve body 6 are dimensioned so that in the vertical position, which is shown in FIG. 1, the weight of the valve body 6 exceeds the spring force of the spring 8, so that the valve body 6 releases the first valve seat 5 and closes the second valve seat 7. In this vertical position of the valve housing 10 (the valve axis A is oriented vertically in this case), the valve 1 is closed for CSF that is present at the inlet 2. In the horizontal position (valve axis A is oriented horizontally) which is shown in FIG. 2 the spring force of the spring 8 predominates, and the second valve seat 7 is released. The valve body rests against the first valve seat 5 and closes valve 1. If the pressure of the CSF exceeds a threshold value, the valve body 6 releases the first valve seat and does not come into contact with the second valve seat 7, so that CSF can be discharged via valve 1.

The combination of valve body 6, spring 8 and first valve seat 5 thus forms a pressure relief valve with a non-return function in this horizontal position. Valve 1 is therefore open for CSF when a threshold value is exceeded. It is secured against back-flow.

In particular, it is provided that the spring 8 engages around the protrusion 40 (and is in particular arranged in the annular gap 14). According to FIGS. 1 and 2, the spring 8 can in particular be designed as a helical spring. Here, the spring 8 can be supported on an inside 12a of the first wall 12 of the valve housing 10, from which the protrusion 40 protrudes into the interior space 4 of the valve housing 10.

In a particularly preferred embodiment of the invention, the valve housing 10 has a circular cross-section (perpendicular to the valve axis A), the circumferential wall 11 having an outer diameter which, according to an example of the invention, is 6.5 mm, the diameter of the interior space 4 or the inner diameter of the wall 11 5.5 mm. The diameter of the valve seats 5, 7 is 1.2 mm in the example.

The length of the path of the valve body 6 in the direction of the valve axis A from valve seat 5 to valve seat 7 is, for example, 1 mm. The valve body 6 is designed in particular as a ball which, in the example mentioned, has a diameter of 5 mm and in particular consists of tungsten carbide with a density of 16.63 g/cm$^3$. The weight of the ball 6 is thus 1.088 g. The weight in water is 0.01023 N (weight minus buoyancy). The spring 8 (in particular helical spring) in the example has a wire diameter of 0.1 mm, a relaxed length of 10 mm, an inner diameter of 2.5 mm and—with 10 turns—a spring constant of 0.005 N/mm. In the horizontal position, the spring 8 has a pretensioned length of 9.6 mm. The spring force is thus 0.002 N. In order to press the ball 6 into the first valve seat 5 in the horizontal position against the force caused by the tilting moment created by the weight, a spring force of at least 0.0019 N is required which consequently is achieved here. In the vertical direction, the weight of the ball 6 compresses the spring 8 by a maximum of 2 mm to a minimum of 8 mm, so that the compressed length of e.g. 8.6 mm selected for the design can be safely achieved. The maximum intracranial pressure of 50 mmHg=7000 Pa pushes the ball 6 with a force of 0.005 N in the direction of the second valve seat 7. The weight of the ball of 0.01023 N minus the closing force of the spring of 0.002 N is 0.00823 N. The ball 6 is thus released from the first valve seat 5 by the intracranial pressure and the weight of the ball and is pressed against the second valve seat and closes it.

In a further preferred embodiment of the invention, the ball has a diameter of 6.5 mm and is made of steel, and the housing has an inner diameter of 7 mm and an outer diameter of 8 mm. The mass of the spring and the diameter of the valve seats are designed as in the example given above.

According to FIG. 3, the valve body 6 can have various designs and can in particular deviate from a spherical geometry.

Thus, according to FIG. 3, the valve body 6 can be cylindrical and have a flat first end surface 60a (dashed line), which is designed to rest against the first valve seat 5, as well as a flat second end surface 60b facing away from the first end surface 60a (dashed line), which is designed to rest on the second valve seat 7.

As an alternative to this, the valve body 6 according to FIG. 3 can have a cylindrical middle section 60 which is arranged between a first end section 61 (dashed line) and a second end section 62 (dashed line) of the valve body 6, wherein the first end section 61 is formed to rest against the first valve seat 5, and wherein the second end section 62 is formed to rest against the second valve seat 7. Here, the two end sections 61, 62 can be curved, hemispherical, frusto-conical or conical, for example.

Furthermore, FIG. 4 shows an embodiment of a valve 1 according to the invention, in which the valve body assembly 600 has a first valve body 6a and a separate second valve body 6b, the first valve body 6a (for example, cylindrical in sections) being configured to rest on the first valve seat 5, and wherein the second (for example spherical) valve body 6b is configured to rest on the second valve seat 7 and/or is made heavier than the first body 6a.

Similarly, embodiments of the valve 1 according to the invention are also possible in which the valve body assembly 600 has a first valve body 6a, one or more second valve bodies 6b and a third valve body 6c, the first valve body 6a (e.g. spherical or cylindrical in sections) is configured to rest against the first valve seat 5, and wherein the third (for example spherical or partially cylindrical) valve body 6c is configured to rest against the second valve seat 7, and wherein the one or more second valve bodies 6b is or are heavier than the first valve body 4 6a and 4/or the third valve body 6c.

Such an embodiment of a valve 1 according to the invention with a valve body assembly 600 formed from three valve bodies 6a, 6b, 6c is shown in FIG. 5 Here, the valve bodies 6a, 6b, 6c are each spherical (other shapes are also conceivable) and arranged next to one another along the valve axis A, the middle second valve body 6b having a larger diameter than the two other valve bodies 6a, 6c, the second valve body 6b is in particular heavier than the first valve body 6a and heavier than the third valve body 6c.

Similar to the configuration shown in FIGS. 1 and 2, it is preferably also provided here that the valve housing 10 has a protrusion 40 protruding into the interior space 4 of the valve housing 10 in the direction of the first valve seat 5, the protrusion 40 forming an annular gap 14 with a circumferential inside 11a of the valve housing 10. The first valve seat 5 lies opposite the protrusion 40 in the direction of the valve axis A and is formed by a circumferential edge area of the inlet 2 of the valve, which can, for example, be conical. In contrast, the second valve seat 7 is provided on an end section of the protrusion 40 facing the first valve seat 5 and can be designed as a circumferential section (e.g., conical step) of a through-opening 3 arranged in the protrusion 40 which forms the outlet 3 of the valve 1.

The three valve bodies 6a, 6b, 6c are arranged along the valve axis A between the two valve seats 5, 7, the first valve body 6a being configured to rest on the first valve seat 5 and the third valve body to rest on the second valve seat 7.

According to FIG. 5, the valve 1 furthermore has a spring device 800 which consists of a first and a second spring 8, 8a, the first spring 8 preferably being a helical spring which engages around the protrusion 40. It is provided that the first spring 8 is supported with a first end section 80 on an inside 12a of the valve housing 10, from which the protrusion 40 protrudes into the interior space 4 of the valve housing 10

In contrast to FIGS. 1 and 2, it is provided here that the first spring 8 contacts the second valve body 6b with a second end section 81 and exerts a first part of a spring force that is to be exerted by the spring device 800 on the valve body assembly 600 towards the first valve seat 5 on the second valve body 6b, the second valve body 6b exerting this first part of the spring force to the first valve body 6a.

Furthermore, in contrast to FIGS. 1 and 2, the spring device 800 has a second spring 8a, the second spring 8a being supported with a first end portion 80a on a step 3a of the through-opening 3 in which the second spring 8a is arranged. The second spring 8a is also preferably designed as a helical spring and has a smaller diameter than the first spring 8. The second spring 8a now contacts the third valve body 6b with a second end section 81a and via a second part of the said spring force in the direction of the first valve seat 5 on the third valve body 6c, which exerts the second part of the spring force via the second valve body 6b to the first valve body 6a.

Figure 6:
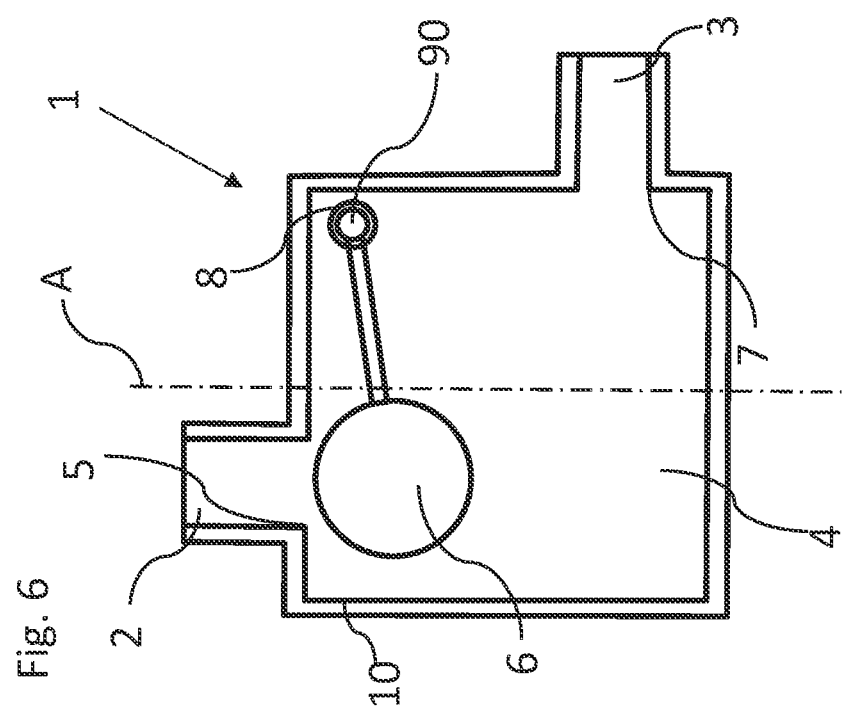
FIG. 6 shows an embodiment of a valve according to the invention with a pivotable valve body.

FIG. 5 shows the valve in a horizontal position (horizontal valve axis A), the entire spring force provided by the two springs 8, 8a pressing the first valve body against the first valve seat 5 so that the valve 1 is closed. This design has the advantage that the second valve seat is closed by the valve body assembly when the valve housing is in an inclined position in which the valve axis encloses an angle with the vertical in the range from 0° to 40°. Furthermore, FIG. 6 shows an embodiment of a valve 1 according to the invention, in which the valve body 6 is pivotably mounted on the valve housing 10 in the interior space 4 (for example via a pivot bearing 90) so that the valve body 6 is pivotable back and forth between the first and the second valve seats 5 and 7. Here, the spring 8, which tries to move or pivot the valve body 6 to the first valve seat, can be designed as a torsion spring 8.

Figure 7:
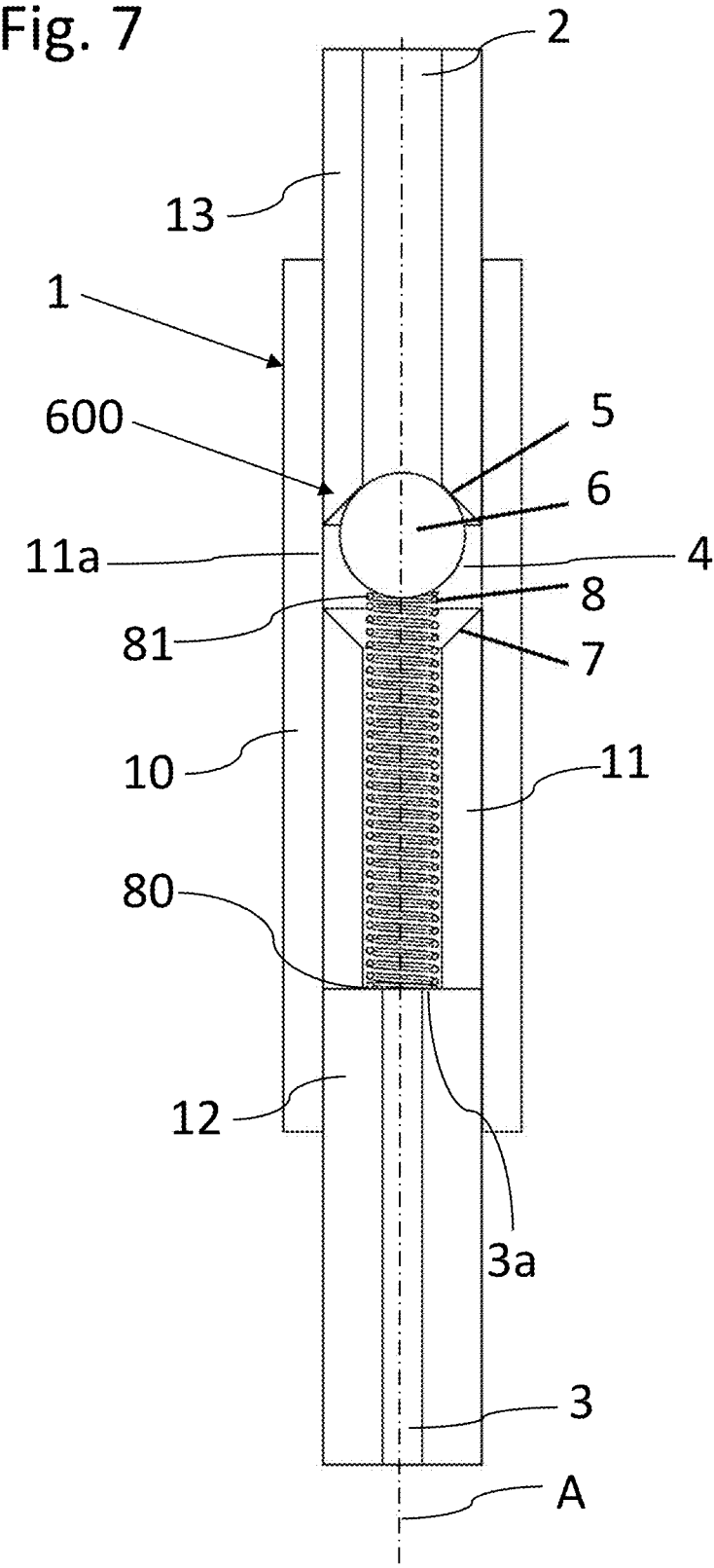
FIG. 7 shows an embodiment of a valve according to the invention, the position of the valve body here being independent of the spatial position of the valve.

FIG. 7 shows a further embodiment of a valve according to the invention. The valve 1 preferably has a valve housing 10 which has an inlet 2 and an outlet 3 as well as an interior space 4. The valve housing 10 extends along a valve axis A, the inlet 2 and the outlet 3 being opposite one another in the direction of the valve axis A.

Between the inlet 2 and the interior space 4 there is a first valve seat 5, which can be closed by a valve body assembly 600, which here consists of the particularly spherical valve body 6. Furthermore, a second valve seat 7, which can also be closed by the valve body 6, is located between the interior space 4 and the outlet 3.

The valve housing 10 has a wall 11 running around it in the circumferential direction of the valve housing 10, which has a circumferential inside 11a facing the interior space 4. The circumferential wall 11 connects a first and a second wall 12, 13 of the valve housing 10, the outlet 3 in particular being provided on the first wall 12 in the form of an elongated through-opening 3, and in particular the inlet 2 on the second wall 13 in form of an elongated through-opening 2.

The valve 1 furthermore has a spring device 800 which is formed by a spring 8, the spring 8 being supported with a first end section 80 on a step 3a of the through-opening 3 which forms the outlet 3 and in which the spring 8 is arranged. The spring 8 is preferably designed as a helical spring and contacts the valve body 6 with a second end section 81 and exerts a spring force on the valve body 6 in the direction of the first valve seat 5.

In the embodiment according to FIG. 7, it is now provided that the mass of the valve body 6 with a given spring device 800 or 8 is selected so that its position relative to the valve seats 5 and 7 is not influenced by the force of gravity on the valve body 6. Accordingly, the function becomes independent of the position relative to the direction of gravity. In the rest position, without a pressure difference between inlet 2 and outlet 3, the valve body 6 is pressed against the first valve seat 5 by the force of the spring 8. In this situation, the valve body 6 acts together with the valve seat 5 as a check valve, so that in the event of a negative pressure difference between inlet 2 and outlet 3, valve 1 does not allow any backward-flow. If the pressure gradient between inlet 2 and outlet 3 is positive and is so high that the force of the spring 8 is overcome, the valve body 6 moves away from the first valve seat 5 and flow through the valve 1 is facilitated. The flow increases as the pressure difference increases. Because of the flow resistance, the valve body 6 is moved in the direction of the second valve seat 7 when the pressure difference increases. When a certain threshold pressure is reached, the valve body 6 contacts the second valve seat 7 and closes it. The valve 1 is now closed and does not allow flow. If the pressure difference falls below a certain second threshold pressure, the force of the spring 8 is higher than the pressure force which presses the valve body 6 against the second valve seat 7, and the valve 1 opens again.

Figure 8:
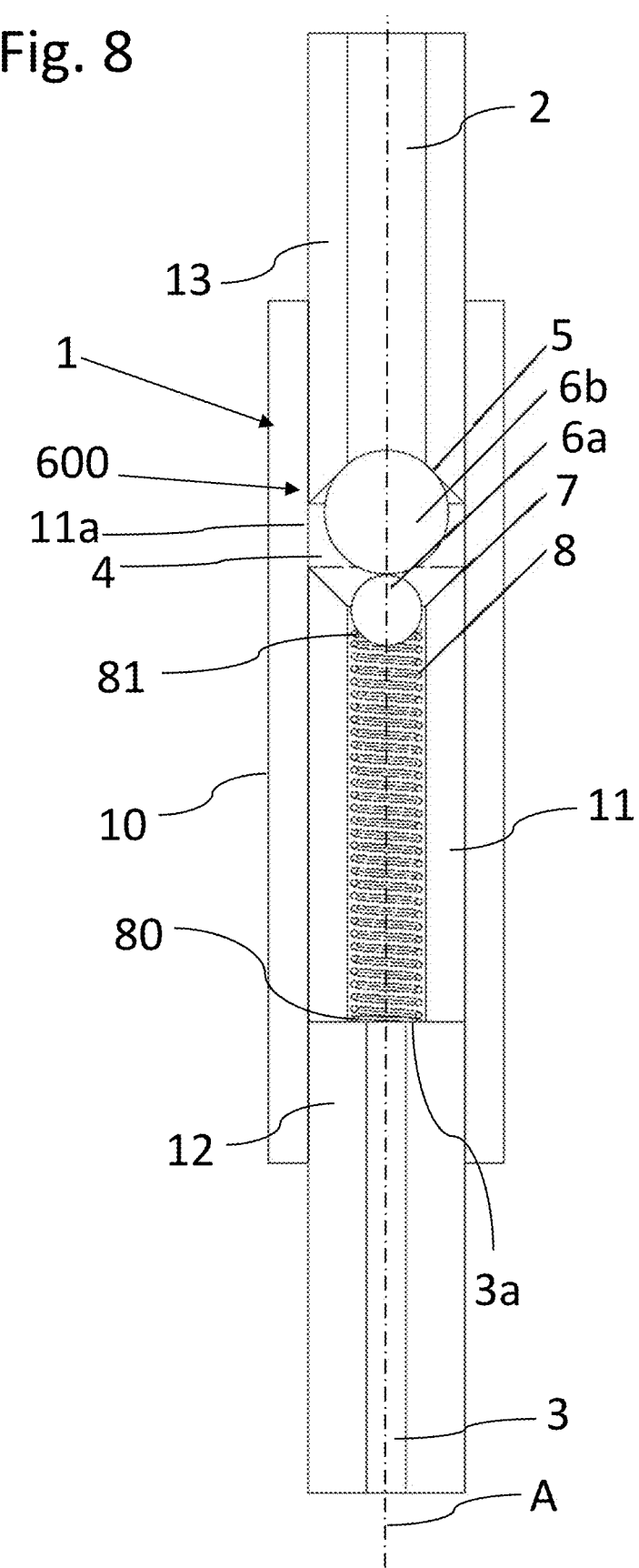
FIG. 8 shows a modification of the embodiment shown in FIG. 7.

FIG. 8 shows a modification of the embodiment shown in FIG. 7, a valve body assembly 600 with a first valve body 6a and a second valve body 6b being provided here instead of the valve body 6, the first valve body 6a corresponding to the valve body 6 of FIG. 7 and in contrast to FIG. 7, the force of the spring 8 does not act directly on the first valve body 6a, but via the second valve body 6b, which in this sense forms a spacer body that contacts the first valve body 6a. The second valve or spacer body 6b has in particular the function of preventing an uppermost turn 8b of the spring 8 from becoming trapped between the second valve seat 7 and the first valve body 6a.

Figure 9:
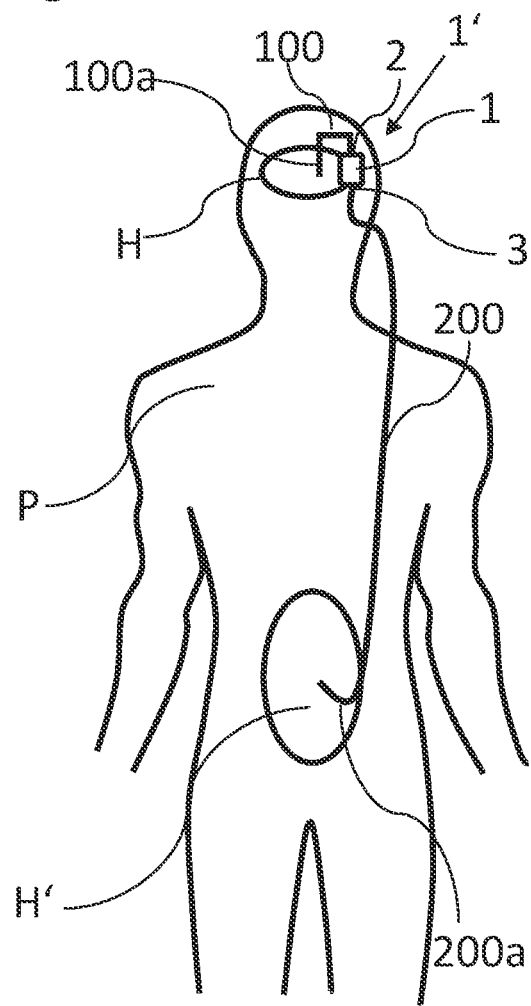
FIG. 9 shows a drainage device according to the invention with a valve according to the invention.

FIG. 9 shows a drainage device 1' according to the invention for draining CSF, which has a valve 1 according to the invention, which can be designed according to one of the exemplary embodiments described herein, as well as a first catheter 100 which has an end portion 100a, which is to be arranged in the ventricle H or in the CSF space of a patient P and which is in flow connection with the inlet 2 of the valve 1. Furthermore, the device 1' has a second catheter 200 which is in flow connection with the outlet 3 of the valve 1 and has an end section 200a to be arranged in a discharge location or cavity H' of the patient P's body.

The invention claimed is:

1. Implantable valve (1) for a drainage device (1') for draining off cerebrospinal fluid, comprising
    a valve housing (10) which extends along a valve axis (A) and comprises an inlet (2) and an outlet (3) as well as an interior space (4) surrounded by the valve housing (10),
    a valve body assembly (600) arranged in the interior space (4), which is movably arranged in the interior space (4) and comprises at least a first valve body (6, 6a, 6b, 6c),
    a first valve seat (5), wherein the valve body assembly (600) is configured to abut the first valve seat (5) to close a flow connection between the inlet (2) and the interior space (4) of the valve housing (10),
    a second valve seat (7), wherein the valve body assembly (6) is configured to abut the second valve seat (7) to close a flow connection between the outlet (3) and the interior space (4) of the valve housing (10),
    wherein when the valve body assembly abuts the first valve seat (5) the flow connection between the outlet (3) and the interior space (4) is open, and wherein when the valve body assembly abuts the second valve seat (7) the flow connection between the inlet (2) and the interior space is open, and
a spring device (800) arranged in the interior space (4) which exerts a spring force on the valve body assembly (600) in the direction of the first valve seat (5).

2. Valve according to claim 1, characterized in that the weight of the valve body assembly (600), in case of a vertical position of the valve housing (10), in which the valve axis (A) extends vertically and the first valve seat (5) is positioned above the second valve seat (7), acts in the direction of the second valve seat (7).

3. Valve according to claim 2, characterized in that the weight of the valve body assembly (600) in the vertical position of the valve housing (10) is greater than the spring force.

4. Valve according to claim 1, characterized in that the spring force in a horizontal position of the valve housing (10), in which the valve axis (A) extends horizontally, is greater than a horizontal component of the weight of the valve body assembly (600).

5. Valve according to claim 1, characterized in that the valve body assembly (600) comprises a second valve body (6b), wherein the first valve body (6a) is configured to rest against the first valve seat (5), and wherein the second valve body (6b) is configured to rest against the second valve seat (7) and/or is heavier than the first valve body (6a).

6. Valve according to claim 1, characterized in that the valve body assembly (6) comprises a second valve body (6b) and a third valve body (6c), the first valve body (6a) is configured for contact with the first valve seat (5) and wherein the third valve body (6c) is configured to rest against the second valve seat (7), and wherein the second valve body (6b) is heavier than the first valve body (6a) and/or the third valve body (6c).

7. Valve according to claim 6, characterized in that the second valve body (6b) is arranged between the first and the third valve body (6a, 6c).

8. Valve according to claim 1, characterized in that the respective valve body (6, 6a, 6b, 6c) of the valve body assembly has a first end section (61) and a second end section (62), wherein in particular the first end section (61) is designed to rest on the first valve seat (5) or to rest on an adjacent valve body, and wherein in particular the second end section (62) is designed to rest on the second valve seat (7) or to rest on an adjacent valve body.

9. Valve according to claim 5, characterized in that a diameter of the second valve body (6b) is greater than a diameter of the first valve body (6a) and/or than a diameter of the third valve body (6b).

10. Valve according to claim 1, characterized in that the respective valve body (6, 6a, 6b, 6c) of the valve body assembly (600) consists of a material which has a density of more than 10 g/cm³.

11. Valve according to claim 1, characterized in that the inlet (2) faces the outlet (3) in the direction of the valve axis (A), and/or that the second valve seat (7) faces the first valve seat (5) in the direction the valve axis (A), and/or that the respective valve body (6, 6a, 6b, 6c) of the valve body assembly (600) is arranged movably in the direction of the valve axis (A) in the interior space (4).

12. Valve according to claim 1, characterized in that the spring device (800) comprises a first spring (8).

13. Valve according to claim 1, characterized in that the valve housing (10) comprises a projection (40) protruding into the interior space (4) in the direction of the first valve seat (5), wherein the projection (40) forms an annular gap (14) together with a circumferential inside (11a) of the valve housing (10), and wherein the second valve seat (7) is provided on an end portion of the projection (40) facing the first valve seat (5), and wherein the first spring (8) engages around the projection (40).

14. Valve according to claim 12, characterized in that the first spring (8) is supported with a first end portion (80) on an inside (12a) of the valve housing (10), and that the projection (40) protrudes into the interior space (4) of the valve housing (10) from the inside (12a) of the valve housing (10).

15. Valve according to claim 14, characterized in that the first spring (8) contacts the at least one first valve body (6) with a second end portion (81) and exerts the spring force on the first valve body (6) in the direction of the first valve seat (5).

16. Valve according to claim 5, characterized in that the first spring (8) contacts the second valve body (6b) with a second end portion (81) and exerts the spring force on the second valve body (6b) in the direction of the first valve seat (5), the second valve body (6b) being configured to transmit the spring force to the first valve body (6a).

17. Valve according to claim 6, characterized in that the first spring (8) contacts the second valve body (6b) with a second end portion (81) and exerts a first part of the spring force on the second valve body (6b) in the direction of the first valve seat (5), the second valve body (6b) being configured to transmit the first part of the spring force to the first valve body (6a).

18. Valve according to claim 17, characterized in that the spring device (800) comprises a second spring (8a), the second spring (8a) being supported with a first end portion (80a) on an inside (12a) of the valve housing (10), and wherein the second spring (8a) contacts the third valve body (6b) with a second end portion (81a) and exerts a second part of the spring force towards the first valve seat (5) on the third valve body (6c), wherein the third valve body (6c) is configured to transmit the second part of the spring force to the first valve body (6a) via the second valve body (6b).

19. Valve according to claim 1, characterized in that that the mass of the valve body assembly (600) and the spring device (800) are selected so that the force of gravity on the valve body assembly (600) does not affect the position of the valve body assembly (600) relative to the first and second valve seats (5, 7).

20. Drainage device (1') for draining cerebrospinal fluid, comprising
a valve (1) according to claim 1,
a first catheter (100) which comprises an end section (100a) which can be arranged in the cerebral ventricle (H) of a patient (P) and which is in flow connection with the inlet (2) of the valve (1), and
a second catheter (200) which is in flow connection with the outlet (3) of the valve (1) and comprises an end section (200a) configured to be arranged in a cavity (H') of the body of the patient (P).

* * * * *